(12) United States Patent
Gee

(10) Patent No.: US 11,174,205 B2
(45) Date of Patent: Nov. 16, 2021

(54) $C_{20}$ 2-SUBSTITUTED ALPHA OLEFINS PRODUCED BY DIMERIZATION OF BRANCHED $C_{10}$ OLEFINS

(71) Applicant: Chevron Phillips Chemical Company LP, The Woodlands, TX (US)

(72) Inventor: Jeffrey C. Gee, Kingwood, TX (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 107 days.

(21) Appl. No.: 16/850,407

(22) Filed: Apr. 16, 2020

(65) Prior Publication Data

US 2021/0323892 A1 Oct. 21, 2021

(51) Int. Cl.
| | |
|---|---|
| *C07C 2/24* | (2006.01) |
| *B01J 31/14* | (2006.01) |
| *B01J 31/38* | (2006.01) |
| *C07C 7/04* | (2006.01) |
| *C07C 11/02* | (2006.01) |

(52) U.S. Cl.
CPC .............. *C07C 2/24* (2013.01); *B01J 31/143* (2013.01); *B01J 31/38* (2013.01); *C07C 7/04* (2013.01); *C07C 11/02* (2013.01); *C07C 2531/14* (2013.01); *C07C 2531/38* (2013.01)

(58) Field of Classification Search
None
See application file for complete search history.

(56) References Cited

U.S. PATENT DOCUMENTS

| | | | |
|---|---|---|---|
| 2,695,327 | A | 11/1954 | Ziegler et al. |
| 4,658,078 | A | 4/1987 | Slaugh et al. |
| 4,973,788 | A | 11/1990 | Lin et al. |
| 5,087,788 | A | 2/1992 | Wu |
| 5,625,105 | A | 4/1997 | Lin et al. |
| 5,659,100 | A | 8/1997 | Lin |
| 5,824,833 | A | 10/1998 | Lin |
| 6,548,723 | B2 | 4/2003 | Bagheri et al. |
| 6,756,514 | B1 | 6/2004 | Barac et al. |
| 7,989,670 | B2 | 8/2011 | Wu et al. |
| 8,207,390 | B2 | 6/2012 | Wu et al. |
| 2008/0146469 | A1 | 6/2008 | Sato et al. |
| 2010/0317904 | A1 | 12/2010 | Small et al. |
| 2015/0099679 | A1 | 4/2015 | Yang et al. |
| 2018/0016204 | A1 | 1/2018 | Coffin et al. |
| 2019/0062234 | A1 | 2/2019 | Chen et al. |

FOREIGN PATENT DOCUMENTS

WO 2017011127 A1 1/2017

OTHER PUBLICATIONS

Deckers, Patrick J. W., et al., "Catalytic Trimerization of Ethene with Highly Active Cyclopentadienyl-Arene Titanium Catalysts," Organometallics, 2002, vol. 21, pp. 5122-5135, American Chemical Society.

(Continued)

*Primary Examiner* — Ali Z Fadhel
(74) *Attorney, Agent, or Firm* — Conley Rose, P.C.

(57) ABSTRACT

Disclosed herein are compositions containing branched $C_{20}$ 2-substituted alpha olefins and processes for making the compositions by dimerization reaction of a $C_{10}$ olefin composition.

22 Claims, 1 Drawing Sheet

(56) References Cited

OTHER PUBLICATIONS

Do, Loi H., et al., "Mechanistic Studies of Ethylene and α-Olefin Co-Oligomerization Catalyzed by Chromium—PNP Complexes," Organometallics, 2012, vol. 31, pp. 5143-5149, American Chemical Society.
Zhou, Yong, et al., "Structural Analysis of Isomers in Commercial Alpha-Olefins with 13C NMR Spectroscopy," Petroleum Processing and Petrochemicals, 2004, vol. 36, No. 5, 15 pages.
Zilbershtein, Timur M., et al., "Decene Formation in Ethylene Trimerization Reaction Catalyzed by Cr-Pyrrole System," Applied Cat A: Gen, 2014, vol. 475, pp. 371-378, Elsevier B.V.
McNaught, Alan D., et al., "Compendium of Chemical Terminology," IUPAC Recommendations, Second edition, 1997, 5 pages, Wiley-Blackwell.

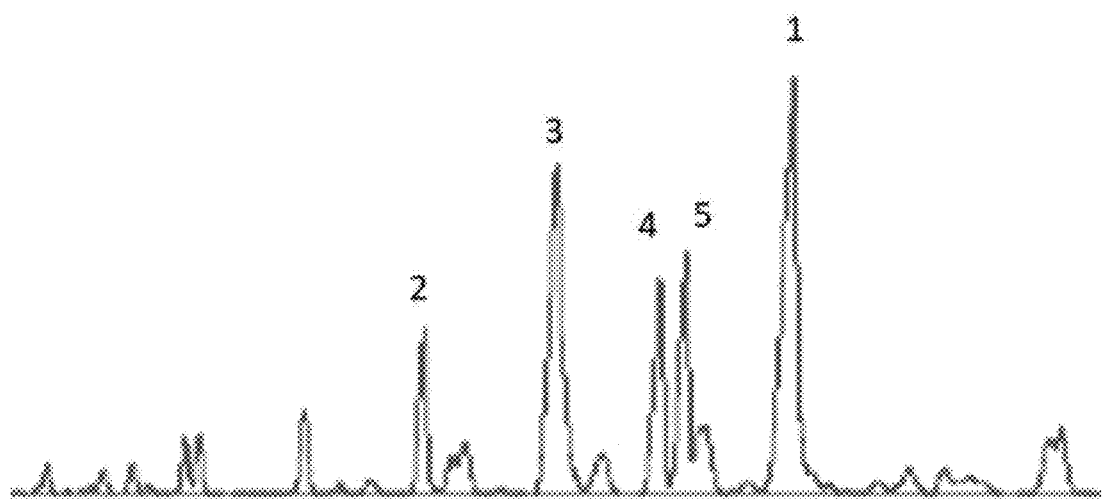

$C_{20}$ 2-SUBSTITUTED ALPHA OLEFINS PRODUCED BY DIMERIZATION OF BRANCHED $C_{10}$ OLEFINS

TECHNICAL FIELD

The present disclosure generally relates to the dimerization of branched $C_{10}$ olefins and the $C_{20}$ 2-substituted alpha olefins produced therefrom.

BACKGROUND

Olefin oligomerization reactions produce olefins using various catalyst systems can be used to direct reactions to particular oligomer products. For example, aluminum, nickel, zirconium, and iron based catalyst systems can be used for the synthesis of oligomer products containing $C_4$ to $C_{30+}$ alpha olefins from ethylene. Chromium based catalyst systems can be used for the selective synthesis of oligomer products containing 1-hexene and/or 1-octene from ethylene. Many applications exist for these oligomer products, including employment as intermediates in the manufacture of detergents, as more environmentally friendly replacements where refined oils might otherwise be used, as monomers or comonomers in the production of polyolefins (e.g., polyethylene), and as intermediates for many other types of products. However, the olefin oligomerization reactions can produce by-products which can be removed from the desired oligomerization product. The oligomerization by-products can have value as commodities, can have value as intermediate chemicals for the synthesis of other higher value products, or can have no value. There is a desire to increase the value of oligomerization by-products.

SUMMARY

Disclosed herein is a composition containing $C_{20}$ 2-substituted alpha olefins. The $C_{20}$ 2-substituted alpha olefins can include 2-(3-methylheptyl)-7-methyl-1-undecene, 2-(4-octyl)-7-methyl-1-undecene, 2-(3-methylheptyl)-5-propyl-1-nonene, 2-(2-ethylhexyl)-7-methyl-1-undecene, 2-(3-methylheptyl)-6-ethyl-1-decene, or any combination thereof. The $C_{20}$ 2-substituted alpha olefins can also include 2-(4-octyl)-5-propyl-1-nonene, 2-(4-octyl)-6-ethyl-1-decene, 2-(2-ethylhexyl)-5-propyl-1-nonene, 2-(2-ethylhexyl)-6-ethyl-1-decene, or any combination thereof. The $C_{20}$ 2-substituted alpha olefins can also include 2-(3-methylheptyl)-1-dodecene, 2-octyl-7-methyl-1-undecene, 2-(4-octyl)-1-dodecene, 2-(3-propylheptyl)-1-decene, 2-(2-ethylhexyl)-1-dodecene, 2-octyl-6-ethyl-1-decene, and 2-octyl-1-dodecene.

Also disclosed herein is a process for producing the composition, the process including 1) contacting i) a $C_{10}$ olefin composition comprising branched $C_{10}$ olefins and ii) a dimerization catalyst or a dimerization catalyst system; and 2) forming a dimerization product. The branched $C_{10}$ olefins can include $C_{10}$ olefins comprising 3-propyl-1-heptene, 4-ethyl-1-octene, methyl-1-nonene, or any combination thereof and the dimerization product can comprise 2-(3-methylheptyl)-7-methyl-1-undecene, 2-(4-octyl)-7-methyl-1-undecene, 2-(3-methylheptyl)-5-propyl-1-nonene, 2-(2-ethylhexyl)-7-methyl-1-undecene, 2-(3-methylheptyl)-6-ethyl-1-decene, or any combination thereof.

BRIEF DESCRIPTION OF THE DRAWINGS

The following FIGURE forms part of the present specification and is included to further demonstrate certain aspects of the present inventions. The inventions may be better understood by reference to the FIGURE in combination with the detailed description of specific aspects presented herein.

The FIGURE illustrates the $C_{20}$ portion of a GC/FID chromatogram of a dimer product of an example $C_{10}$ olefin composition comprising branched $C_{10}$ olefins.

DETAILED DESCRIPTION

Illustrative aspects of the subject matter claimed herein will now be disclosed. In the interest of clarity, not all features of an actual implementation are described in this specification. It can be appreciated that in the development of any such actual aspect, numerous implementation-specific decisions must be made to achieve the developers' specific goals, such as compliance with system-related and business-related constraints, which can vary from one implementation to another. Moreover, it can be appreciated that such a development effort, even if complex and time-consuming, would be a routine undertaking for those of ordinary skill in the art having the benefit of this disclosure.

In the description herein, various ranges and/or numerical limitations can be expressly stated below. It should be recognized that unless stated otherwise, it is intended that endpoints are to be interchangeable. Further, any ranges include iterative ranges of like magnitude falling within the expressly stated ranges or limitations.

Furthermore, various modifications can be made within the scope of the invention as herein intended, and aspects of the invention can include combinations of features other than those expressly claimed. In particular, flow arrangements other than those expressly described herein are within the scope of the invention.

Unless otherwise specified, the terms "contact" and "combine," and their derivatives, can refer to any addition sequence, order, or concentration for contacting or combining two or more components of the disclosed embodiments. Combining or contacting of dimerization components can occur in one or more reaction zones under suitable contact conditions such as temperature, pressure, contact time, flow rates, etc.

Within this specification, the word "reactor" refers to a single piece of equipment, such as, for example, a vessel, in which a reaction takes place, but excludes any associated equipment such as piping, pumps, and the like which is external to the vessel. Examples of reactors include stirred tank reactors (e.g., a continuous stirred tank reactor), plug flow reactors, or any other type of reactor. Within this specification "reaction zone" refers to any portion of equipment in which a desired reaction occurs, including but not limited to, a reactor, associated piping, associated pumps, and any other associated equipment. It should be noted that in some cases a "reactor" can also be a "reaction zone". The terms "reactor" and "reaction zone" can be qualified to refer to more specific "reactors" and "reaction zones" by use of additional qualifying terms. For example, the use of the term "dimerization reactor" and "dimerization reaction zone" indicates that the desired reaction within the reactor and/or reaction zone is a dimerization reaction.

Within this specification, term "reaction zone" refers to the portion of a process, the associated equipment and associated process lines where all the necessary reaction components and reaction conditions are present such that the reaction can occur at a desired rate. That is to say that the reaction zone begins where the necessary reaction components and reaction conditions are present to maintain the reaction within 25 percent of the average reaction rate and the reaction system ends where the conditions do not maintain a reaction rate within 25 percent of the average reaction rate (based upon a volume average of the reaction rate of the reaction system). For example, in terms of a dimerization process, the reaction zone begins at the point where sufficient feedstock and active catalyst system is present under the sufficient reaction conditions to maintain dimerization product production at the desired rate and the reaction zone ends at a point where either the catalyst system is deactivated, sufficient feedstock is not present to sustain dimerization product production, or other reaction conditions are not sufficient to maintain the dimerization product production or the desired dimerization product production rate. Within this specification the "reaction zone" can comprise one or more reactor zone, one or more reactors, and associated equipment where all the necessary reaction components and reaction conditions are present such that the reaction can occur at a desired rate. The use of the term "dimerization reaction zone" indicates that the desired reaction within the reaction zone is a dimerization reaction.

Unless otherwise indicated, the definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition can be applied. To the extent that any definition or usage provided by any document incorporated herein by reference conflicts with the definition or usage provided herein, the definition or usage provided herein controls.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to hexene includes 1-hexene, 2-hexene, 3-hexene, and any other hydrocarbon having 6 carbon atoms (linear, branched or cyclic) and a single carbon carbon double bond. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure of a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, or tertiary carbon atom, respectively, of an alkane. The n-alkyl group can be derived by removal of a hydrogen atom from a terminal carbon atom of a linear alkane.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from the carbon atom of an aliphatic compound. Aliphatic compounds and therefore aliphatic groups can contain organic functional group(s) and/or atom(s) other than carbon and hydrogen.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc. . . . carbon-carbon double bonds can be identified by use of the term "mono," "di," "tri," etc. . . . within the name of the olefin. The olefins can be further identified by the position of the carbon-carbon double bond(s).

The term "alkene" whenever used in this specification and claims refers to a linear or branched aliphatic hydrocarbon olefin that has one or more carbon-carbon double bonds. Alkenes having only one, only two, only three, etc. . . . such multiple bonds can be identified by use of the term "mono," "di," "tri," etc. . . . within the name. Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of other carbon-carbon double bonds unless explicitly indicated.

The term "reaction zone effluent," and it derivatives (e.g., dimerization reaction zone effluent) generally refers to all the material which exits the reaction zone through a reaction zone outlet/discharge which discharges a reaction mixture and can include reaction zone feed(s) (e.g., olefin, catalyst system or catalyst system components, and/or solvent), and/or reaction product (e.g., dimerization product and dimerization by-product). The term "reaction zone effluent" and its derivatives can be qualified to refer to certain portions by use of additional qualifying terms. For example, while reaction zone effluent refers to all material which exits the reaction zone through the reaction zone outlet/discharge, a reaction zone dimerization product effluent refers to only the dimerization product within the reaction zone effluent.

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" any recited maximum value for the feature disclosed herein.

Within this disclosure the normal rules of organic nomenclature prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. References to compounds or groups having substitution at positions in addition to the indicated position can be referenced using comprising or some other alternative language. For example, a reference to a phenyl group comprising a substituent at the 4 position refers to a phenyl group having a non-hydrogen substituent group at the 4 position and hydrogen or any non-hydrogen group at the 2, 3, 5, and 6 positions.

Processes and/or, methods described herein can utilize steps, features, and compounds which are independently described herein. The process and/or methods described herein may or may not utilize step identifiers (e.g., 1), 2), etc., a), b), etc., i), ii), etc., or first, second etc., among others), features (e.g., 1), 2), etc., a), b), etc., i), ii), etc., or first, second etc., among others), and/or compound and/or composition identifiers (e.g., 1), 2), etc., a), b), etc., i), ii), etc., or first, second etc., among others). However, it should be noted that processes and/or methods described herein can have multiple steps, features (e.g. reagent ratios, formation conditions, among other considerations), and/or multiple compounds and/or composition using no descriptor or sometimes having the same general identifier. Consequently, it should be noted that the processes and/or methods described herein can be modified to use an appropriate step or feature identifier (e.g., 1), 2), etc., a), b), etc., i), ii), etc., or first, second etc., among others), feature identifier features (e.g., 1), 2), etc., a), b), etc., i), ii), etc., or first, second etc., among others), and/or compound identifier (e.g., first, second, etc.) regardless of step, feature, and/or compound identifier utilized in the a particular statement, aspect, and/or embodiment described herein and that step or feature identifiers can be added and/or modified to indicate individual different steps/features/compounds utilized within the process and/or methods without detracting from the general disclosure.

Terms that indicate the state of matter, such as gas, liquid, solid, and their equivalents, refer to the state of matter at normal temperature and normal pressure: i.e., a temperature of 20° C. (293.15 K, 68° F.) and an absolute pressure of 1 atm (14.696 psi, 101.325 kPa). As used herein, the term "normal conditions" refer to conditions of normal temperature (i.e., 20° C., 293.15 K, 68° F.) and normal pressure (e.g., 1 atm, 14.696 psi, 101.325 kPa).

Disclosed herein are compositions having $C_{20}$ 2-substituted alpha olefins and the processes for producing the compositions. Generally, the processes for producing the composition comprising $C_{20}$ 2-substituted alpha olefins can comprise 1) contacting i) a $C_{10}$ olefin composition and ii) a dimerization catalyst or a dimerization catalyst system; and 2) forming a dimerization product comprising $C_{20}$ 2-substituted alpha olefins. In an aspect, the dimerization product can comprise $C_{20}$ 2-substituted alpha olefins. The $C_{20}$ 2-substituted alpha olefins can be used in various applications, such as a feedstock for making alkenyl succinic anhydride (e.g., via reaction with maleic anhydride). The alkenyl succinic anhydrides (and their derivatives) produced from the $C_{20}$ 2-substituted alpha olefins can be used as a paper sizing agent, or as a lube oil additive, among other uses.

The $C_{10}$ olefin composition, the dimerization catalyst/dimerization catalyst system, the dimerization product, the $C_{20}$ 2-substituted alpha olefins, dimerization process steps, and dimerization process conditions for forming the dimerization product are independently described herein and these independent descriptions can be utilized without limitation and in any combination to further describe the processes for producing the dimerization product (e.g., the $C_{20}$ 2-substituted alpha olefins) described herein.

In an aspect, the $C_{10}$ olefin composition which can be utilized in the processes described herein can comprise branched $C_{10}$ olefins; or alternatively, branched $C_{10}$ alpha olefins. In other aspects, and in addition to the branched $C_{10}$ olefins (or branched $C_{10}$ alpha olefins), the $C_{10}$ olefin composition can further comprise linear $C_{10}$ olefins (i.e., a mixture comprising branched $C_{10}$ olefins (or branched $C_{10}$ alpha olefins) and linear $C_{10}$ olefins). In an aspect, the linear $C_{10}$ olefins can be linear alpha olefins. The identity of the branched $C_{10}$ olefins (or branched $C_{10}$ alpha olefins), the amount(s) of each branched $C_{10}$ olefins (or branched $C_{10}$ alpha olefins), the identity of linear $C_{10}$ olefins, the amounts of each linear $C_{10}$ olefins which can be present in the $C_{10}$ olefin composition are independently described herein and these independent descriptions can be utilized in any combination to further describe the $C_{10}$ olefins present in the $C_{10}$ olefin composition utilized for the processes described herein.

In an aspect, the $C_{10}$ olefin composition which can be utilized in the processes disclosed herein can comprise at least 50 mole %, 60 mole %, 65 mole %, 70 mole %, 75 mole %, 80 mole %, 85 mole %, 90 mole %, or 95 mole % branched $C_{10}$ olefins (or branched $C_{10}$ alpha olefins); alternatively or additionally, less than or equal to 99.5 mole %, 99 mole %, 98 mole %, 97 mole %, 95 mole %, 92 mole %, or 90 mole % branched $C_{10}$ olefins (or branched $C_{10}$ alpha olefins). Generally, the $C_{10}$ olefin composition can comprise branched $C_{10}$ olefins (or branched $C_{10}$ alpha olefins) ranging from any minimum branched $C_{10}$ olefins (or branched $C_{10}$ alpha olefins) content disclosed herein to any maximum branched $C_{10}$ olefins (or branched $C_{10}$ alpha olefins) content disclosed herein. For example, in some aspects, the $C_{10}$ olefin composition can comprise from 50 mole % to 99.5 mole %, from 65 mole % to 99 mole %, from 75 mole % to 99 mole %, from 85 mole % to 97 mole %, from 80 mole % to 95 mole %, from 70 mole % to 95 mole %, or from 75 mole % to 90 mole % branched $C_{10}$ olefins (or branched $C_{10}$ alpha olefins). Other ranges for the branched $C_{10}$ olefins (or branched $C_{10}$ alpha olefins) within the $C_{10}$ olefin composition are readily apparent to those skilled in the art with the aid of this disclosure.

In an aspect, the branched $C_{10}$ olefins (or branched $C_{10}$ alpha olefins) of the $C_{10}$ olefin composition can comprise, or can consist essentially of 3-propyl-1-heptene, 4-ethyl-1-octene, 5-methyl-1-nonene, or any combination thereof; alternatively, 3-propyl-1-heptene, 4-ethyl-1-octene, and 5-methyl-1-nonene; or alternatively, 3-propyl-1-heptene, 4-ethyl-1-octene, 5-methyl-1-nonene, and 2-butyl-1-hexene. In an aspect, the branched $C_{10}$ olefins (or branched $C_{10}$ alpha olefins) of the $C_{10}$ olefin composition can comprise i) at least 8 mole %, at least 9 mole %, at least 10 mole %, at least 11 mole %, at least 12 mole %, or at least 13 mole % 3-propyl-1-heptene, ii) at least 6 mole %, at least 7 mole %, at least 8 mole %, at least 9 mole %, at least 10 mole %, or at least 11 mole % 4-ethyl-1-octene, and/or iii) at least 20 mole %, at least 22 mole %, at least 24 mole %, at least 26 mole %, at least 28 mole %, or at least 30 mole % 5-methyl-1-nonene; alternatively, i) at least 8 mole %, at least 9 mole %, at least 10 mole %, at least 11 mole %, at least 12 mole %, or at least 13 mole % 3-propyl-1-heptene, ii) at least 6 mole %, at least 7 mole %, at least 8 mole %, at least 9 mole %, at least 10 mole %, and/or at least 11 mole % 4-ethyl-1-octene, iii) at least 20 mole %, at least 22 mole %, at least 24 mole %, at least 26 mole %, at least 28 mole %, or at least 30 mole % 5-methyl-1-nonene, and iv) at least 3 mole %, at least 4 mole %, at least 5 mole %, at least 6 mole %, at least 7 mole %, or at least 8 mole % 2-butyl-1-hexene. In another aspect, the branched $C_{10}$ olefins (or branched $C_{10}$ alpha olefins) of the $C_{10}$ olefin composition can comprise i) from 8 mole % to 35 mole %, from 10 mole % to 35 mole %, from 11 mole % to 30 mole %, from 12 mole % to 28 mole %, from 13 mole % to 26 mole %, or from 14 mole % to 24 mole % 3-propyl-1-heptene, ii) from 7 mole % to 30 mole %, from 7 mole % to 30 mole %, from 8 mole % to 25 mole %, from 9 mole % to 23 mole %, from 10 mole % to 22 mole %, or from 11 mole % to 21 mole % 4-ethyl-1-octene, and/or iii) from 24 mole % to 65 mole %, from 24 mole % to 65 mole %, from 26 mole % to 60 mole %, from 28 mole % to 55 mole %, from 30 mole % to 50 mole %, or from 32 mole % to 48 mole % 5-methyl-1-nonene; alternatively, i) from 8 mole % to 35 mole %, from 10 mole % to 35 mole %, from 11 mole % to 30 mole %, from 12 mole % to 28 mole %, from 13 mole % to 26 mole %, or from 14 mole % to 24 mole % 3-propyl-1-heptene, ii) from 7 mole % to 30 mole %, from 7 mole % to 30 mole %, from 8 mole % to 25 mole %, from 9 mole % to 23 mole %, from 10 mole % to 22 mole %, or from 11 mole % to 21 mole % 4-ethyl-1-octene, iii) from 24 mole % to 65 mole %, from 24 mole % to 65 mole %, from 26 mole % to 60 mole %, from 28 mole % to 55 mole %, from 30 mole % to 50 mole %, or from 32 mole % to 48 mole % 5-methyl-1-nonene, and/or iv) from 3 mole % to 25 mole %, from 4 mole % to 22 mole %, from 5 mole % to 20 mole %, from 6 mole % to 18 mole %, or from 7 mole % to 16 mole % 2-butyl-1-hexene.

In an aspect, the $C_{10}$ olefin composition which can be utilized in the processes disclosed herein can comprise a maximum of 50 mole %, 40 mole %, 30 mole %, 25 mole %, 20 mole %, 15 mole % or 10 mole % linear $C_{10}$ olefins (or linear $C_{10}$ alpha olefins); alternatively or additionally, the $C_{10}$ olefin composition can comprise a minimum of 0 mole %, 0.5 mole %, 1 mole %, 1.5 mole %, 2 mole %, or 2.5 mole % linear $C_{10}$ olefins (or linear $C_{10}$ alpha olefins). Generally, the $C_{10}$ olefin composition can comprise linear $C_{10}$ olefins (or linear $C_{10}$ alpha olefins) ranging from any minimum linear $C_{10}$ olefin (or linear $C_{10}$ alpha olefins) content disclosed herein to any maximum linear $C_{10}$ olefin (or linear $C_{10}$ alpha olefins) content disclosed herein. For example, in some non-limiting aspects, the $C_{10}$ olefin composition can comprise from 0 mole % to 50 mole %, from 0.5 mole % to 40 mole %, from 1 mole % to 30 mole %, from 1.5 mole % to 25 mole %, from 2 mole % to 25 mole %, or from 2.5 mole % to 20 mole % linear $C_{10}$ olefins (or linear $C_{10}$ alpha olefins). Other ranges for the linear $C_{10}$ olefins (or linear $C_{10}$ alpha olefins) within the $C_{10}$ olefin composition are readily apparent to those skilled in the art with the aid of this disclosure.

In an aspect, the linear $C_{10}$ olefins (or linear $C_{10}$ alpha olefins) present in the $C_{10}$ olefin composition can comprise (or consist essentially of, or consist of) 1-decene; alternatively, 4- and/or 5-decene; or alternatively, 1-decene, and 4- and/or 5-decene. In some aspects, the $C_{10}$ olefin composition can comprise a maximum of 40 mole %, 30 mole %, 25 mole %, 20 mole %, 15 mole % or 10 mole % 1-decene; alternatively, or additionally, the $C_{10}$ olefin composition can comprise a minimum of 0 mole %, 0.5 mole %, 1 mole %, 1.5 mole %, 2 mole %, or 2.5 mole % 1-decene. Generally, the $C_{10}$ olefin composition can comprise 1-decene ranging from any minimum 1-decene content disclosed herein to any maximum 1-decene content disclosed herein. For example, in some non-limiting aspects, the $C_{10}$ olefin composition can comprise from 0 mole % to 40 mole %, 0.5 mole % to 30 mole %, 1 mole % to 25 mole %, 1 mole % to 20 mole %, 1 mole % to 15 mole %, 1.5 mole % to 15 mole %, or 1.5 mole to 10 mole % 1-decene. In other aspects, the $C_{10}$ olefin composition can comprise a maximum of 25 mole %, 22.5 mole %, 20 mole %, 19 mole %, or 18 mole % 4- and/or 5-decene; alternatively or additionally, $C_{10}$ olefin composition can comprise a minimum of 0 mole %, 1 mole %, 2 mole %, 3 mole %, 4 mole %, or 5 mole % 4- and/or 5-decene. For example, in some non-limiting aspects, the $C_{10}$ olefin composition can comprise from 0 mole % to 25 mole %, 1 mole % to 20 mole %, 2 mole % to 19 mole %, 3 mole % to 18 mole %, 4 mole % to 17 mole %, 4 mole % to 18 mole %, or 5 mole % to 18 mole % 4- and/or 5-decene. Other ranges for 1-decene, and 4- and/or 5-decene within the $C_{10}$ olefin composition are readily apparent to those skilled in the art with the aid of this disclosure.

In some aspects, the $C_{10}$ olefin composition is a $C_{10}$ olefin composition containing $C_{10}$ olefins as described herein that is substantially devoid of heteroatomic compounds. Examples of heteroatomic compounds include amines (e.g., pyrroles), peroxides, and alcohols (e.g., ethyl hexanol). "Substantially devoid of heteroatomic compounds" as used herein means a concentration of heteroatomic compounds which is less than 1, 0.1, 0.01, 0.001, or 0.0001 mass % based on a total mass of the $C_{10}$ olefin composition.

Methods for making/obtaining a $C_{10}$ olefin composition containing the above-described $C_{10}$ olefins are disclosed in U.S. Patent Application Publication No. 2018/0016204.

In an aspect, any suitable dimerization catalyst or dimerization catalyst system which can produce the desired the $C_{20}$ 2-substituted alpha olefins can be used in the process to produce the $C_{20}$ 2-substituted alpha olefins. Non-limiting examples of dimerization catalysts and dimerization catalyst systems which can be used can comprise i) an alkylaluminum compound, ii) a zirconium compound, or iii) a metallocene compound, alternatively, i) an alkylaluminum compound, and/or ii) a zirconium compound; alternatively, i) an alkylaluminum compound, or ii) a metallocene compound; alternatively, an alkylaluminum compound, alternatively, a zirconium compound, or alternatively, a metallocene compound.

In an aspect, the $C_{20}$ 2-substituted alpha olefins can be produced using a catalyst or catalyst system comprising (or consisting essentially of, or consisting of) an alkylaluminum compound. In an aspect, the alkylaluminum compound can comprise, or consist essentially of, a trialkylaluminum compound. In an aspect, the trialkylaluminum compound can comprise, or consist essentially of, singly or in any combination, triethylaluminum, triethylaluminum, tripropylaluminum (e.g., tri-n-propylaluminum and/or tri-2-propylaluminum), tributylaluminum (e.g., tri-n-butylaluminum, tri-2-butylaluminum, and/or tri-t-butyl aluminum), trihexylaluminum, or trioctylaluminum. Other suitable alkylaluminum compounds (and trialkylaluminum compounds) are known to those skilled in the art. Any suitable conditions for dimerizing the alpha olefins with the catalyst or catalyst system comprising (or consisting essentially of, or consisting of) an alkylaluminum compound can be employed.

In an aspect, the $C_{20}$ 2-substituted alpha olefins can be produced using a dimerization catalyst or dimerization catalyst system comprising a zirconium compound. In an aspect, the catalyst system can comprise a zirconium compound and an alkylaluminum compound; alternatively, can comprise a zirconium compound and an aluminoxane; or alternatively can comprise a zirconium compound, an alkylaluminum compound, and an aluminoxane. Generally, the zirconium compound can be any compound that when combined with the alkylaluminum compound (or aluminoxane, or alkylaluminum compound and aluminoxane) can dimerize an alpha olefin to produce a 2-substituted alpha olefin. In an aspect, the zirconium compound can be a zirconium halide compound; alternatively, a dicyclopentadienyl zirconium halide compound; alternatively, a dicyclopentadienyl zirconium dihalide; or alternatively, dicyclopentadienyl zirconium dichloride. In an aspect, the alkylaluminum compound which can be utilized with the zirconium compound of the dimerization catalyst systems disclosed herein can comprise an alkylaluminum dihalide, an alkylaluminum sesquihalide, an dialkylaluminum halide, a trialkylaluminum compound, or any combination thereof; alternatively, alkylaluminum dihalide; alternatively, an alkylaluminum sesquihalide; alternatively, an dialkylaluminum halide; or alternatively, a trialkylaluminum compound. In an aspect, the aluminoxane which can be utilized with the zirconium compound of the dimerization catalyst systems disclosed herein can comprise (or consist essentially of, or consist of) methylaluminoxane (MAO), ethylaluminoxane, a modified methylaluminoxane (MMAO), n-propylaluminoxane, iso-propyl-aluminoxane, n-butylaluminoxane, sec-butylaluminoxane, iso-butylaluminoxane, t-butylaluminoxane, 1-pentylaluminoxane, 2-pentylaluminoxane, 3-pentyl-aluminoxane, iso-pentyl-aluminoxane, neopentylaluminoxane, or any combination thereof. In one particular aspect, the dimerization catalyst system can comprise (or consist essentially of, or consist of) dicyclopentadienyl zirconium dichloride and any aluminoxane disclosed herein.

In an aspect, the $C_{20}$ 2-substituted alpha olefins can be produced using a catalyst system comprising a metallocene compound. In an aspect, the catalyst system can comprise a metallocene compound and an aluminoxane, or a metallocene compound, a non-coordinating anion activator, and an alkylaluminum compound; alternatively, a metallocene compound and an aluminoxane; or alternatively, a metallocene compound, a non-coordinating anion activator, and an alkylaluminum compound. Generally, the metallocene compound can be any metallocene compound that, when utilized in the presence of the other catalyst system components, can dimerize the alpha olefins to 2-substituted alpha olefins. Suitable metallocenes which can be utilized the dimerization catalyst system comprising a metallocene are disclosed in U.S. Pat. Nos. 6,548,723, 7,989,670, and 8,207,390; U.S. Patent Application Publication Nos. 2010/0317904 and 2008/0146469; among other documents. Suitable aluminoxane and/or alkylaluminum compounds which can be utilized the dimerization catalyst system comprising a metallocene are disclosed herein and in U.S. Pat. Nos. 6,548,723, 7,989,670, and 8,207,390; U.S. Patent Application Publication Nos. 2010/0317904, 2008/0146469; among other documents. Suitable a non-coordinating anion activator which can be utilized the dimerization catalyst system comprising a metallocene are disclosed in U.S. Pat. Nos. 7,989,670 and 8,207,390; U.S. Patent Application Publication No. 2010/0317904; among other documents.

A product, or a portion of the product, of the process(es) described herein is a composition comprising $C_{20}$ 2-substituted alpha olefins. In an embodiment, the composition comprising $C_{20}$ 2-substituted alpha olefins, can comprise at least 50, 60, 70, 75, 80, 85, 90, or 95 mole % $C_{20}$ 2-substituted alpha olefins. Description of the $C_{20}$ 2-substituted alpha olefins is divided into three groups; a first group of $C_{20}$ 2-substituted alpha olefins, a second group of $C_{20}$ 2-substituted alpha olefins, and a third group of $C_{20}$ 2-substituted alpha olefins. The description of the $C_{20}$ 2-substituted alpha olefins of the composition comprising $C_{20}$ 2-substituted alpha olefins can include one or more of the $C_{20}$ 2-substituted alpha olefin(s) selected from the first group; alternatively, one or more of branched $C_{20}$ 2-substituted alpha olefins selected from the first group and one or more of the $C_{20}$ 2-substituted alpha olefins selected from the second group; or alternatively, one or more of the branched $C_{20}$ 2-substituted alpha olefin(s) selected from the first group, one or more of the $C_{20}$ 2-substituted alpha olefin(s) selected from the second group, and one or more of the $C_{20}$ 2-substituted alpha olefin(s) selected from the third group.

In aspects, the $C_{20}$ 2-substituted alpha olefins of the first group can include 2-(3-methylheptyl)-7-methyl-1-undecene, 2-(4-octyl)-7-methyl-1-undecene, 2-(3-methylheptyl)-5-propyl-1-nonene, 2-(2-ethylhexyl)-7-methyl-1-undecene, 2-(3-methylheptyl)-6-ethyl-1-decene, or any combination thereof. In one aspect, the $C_{20}$ 2-substituted alpha olefins can comprise, only one, only two, only three, or only four, of 2-(3-methylheptyl)-7-methyl-1-undecene, 2-(4-octyl)-7-methyl-1-undecene, 2-(3-methylheptyl)-5-propyl-1-nonene, 2-(2-ethylhexyl)-7-methyl-1-undecene, and 2-(3-methylheptyl)-6-ethyl-1-decene. In another aspect, the $C_{20}$ 2-substituted alpha olefins can comprise 2-(3-methylheptyl)-7-methyl-1-undecene, 2-(4-octyl)-7-methyl-1-undecene, 2-(3-methylheptyl)-5-propyl-1-nonene, 2-(2-ethylhexyl)-7-methyl-1-undecene, and 2-(3-methylheptyl)-6-ethyl-1-decene.

In an aspect, the $C_{20}$ 2-substituted alpha olefins can include any minimum amount of 2-(3-methylheptyl)-7-methyl-1-undecene, 2-(4-octyl)-7-methyl-1-undecene, 2-(3-methylheptyl)-5-propyl-1-nonene, 2-(2-ethylhexyl)-7-methyl-1-undecene, and/or 2-(3-methylheptyl)-6-ethyl-1-decene disclosed herein. In an aspect, 2-(3-methylheptyl)-7-methyl-1-undecene, when present, can comprise at least 10, 11, 12, 13, 14, 15, 16, 17, 18, 19, or 20 mole % of the $C_{20}$ 2-substituted alpha olefins; alternatively or additionally, a maximum of (less than or equal to) 50, 45, 40, 38, 36, 32, or 30 mole % of the $C_{20}$ 2-substituted alpha olefins. In another aspect, 2-(3-methylheptyl)-7-methyl-1-undecene, when present, can comprise from any minimum mole % of the $C_{20}$ 2-substituted alpha olefins described herein to any maximum mole % of the $C_{20}$ 2-substituted alpha olefins described herein; for example from 10 mole % to 50 mole %, from 12 to 45 mole %, from 15 to 40 mole %, from 18 to 38 mole %, from 17 to 36 mole %, from 18 to 34 mole %, from 19 to 32 mole %, or from 20 to 30 mole % 2-(3-methylheptyl)-7-methyl-1-undecene. In an aspect, 2-(4-octyl)-7-methyl-1-undecene, when present, can comprise at least 3, 4, 5, 6, or 7 mole % of the $C_{20}$ 2-substituted alpha olefins; alternatively or additionally, a maximum of (less than or equal to) 25, 21, 19, 17, 15 mole % of the $C_{20}$ 2-substituted alpha olefins. In another aspect, 2-(4-octyl)-7-methyl-1-undecene, when present, can comprise from any minimum mole % of the $C_{20}$ 2-substituted alpha olefins described herein to any maximum mole % of the $C_{20}$ 2-substituted alpha olefins described herein; for example from 3 mole % to 25 mole %, from 4 to 21 mole %, from 5 to 19 mole %, from 6 to 17 mole %, or from 7 to 15 mole % 2-(4-octyl)-7-methyl-1-undecene. In an aspect, 2-(3-methylheptyl)-5-propyl-1-nonene, when present, can comprise at least 3, 4, 5, 6, or 7 mole % of the $C_{20}$ 2-substituted alpha olefins; alternatively or additionally, a maximum of (less than or equal to) 25, 21, 19, 17, 15 mole % of the $C_{20}$ 2-substituted alpha olefins. In another aspect, 2-(3-methylheptyl)-5-propyl-1-nonene, when present, can comprise from any minimum mole % of the $C_{20}$ 2-substituted alpha olefins described herein to any maximum mole % of the $C_{20}$ 2-substituted alpha olefins described herein; for example from 3 mole % to 25 mole %, from 4 to 21 mole %, from 5 to 19 mole %, from 6 to 17 mole %, or from 7 to 15 mole % 2-(3-methylheptyl)-5-propyl-1-nonene; In an aspect, 2-(2-ethylhexyl)-7-methyl-1-undecene, when present, can comprise at least 3, 4, 5, 6, or 7 mole % of the $C_{20}$ 2-substituted alpha olefins; alternatively or additionally, a maximum of (less than or equal to) 25, 21, 19, 17, 15 mole % of the $C_{20}$ 2-substituted alpha olefins. In another aspect, 2-(2-ethylhexyl)-7-methyl-1-undecene, when present, can comprise from any minimum mole % of the $C_{20}$ 2-substituted alpha olefins described herein to any maximum mole % of the $C_{20}$ 2-substituted alpha olefins described herein; for example from 3 mole % to 25 mole %, from 4 to 21 mole %, from 5 to 19 mole %, from 6 to 17 mole %, or from 7 to 15 mole % 2-(2-ethylhexyl)-7-methyl-1-undecene. In an aspect, 2-(3-methylheptyl)-6-ethyl-1-decene, when present, can comprise at least 5, 6, or 7 mole % of the $C_{20}$ 2-substituted alpha olefins; alternatively or additionally, a maximum of (less than or equal to) 25, 21, 19, 17, 15 mole % of the $C_{20}$ 2-substituted alpha olefins. In another aspect, 2-(3-methylheptyl)-6-ethyl-1-decene, when present, can comprise from any minimum mole % of the $C_{20}$ 2-substituted alpha olefins described herein to any maximum mole % of the $C_{20}$ 2-substituted alpha olefins described herein; for example from 3 mole % to 25 mole %, from 4 to 21 mole %, from 5 to 19 mole %, from 6 to 17 mole %, or from 7 to 15 mole % 2-(3-methylheptyl)-6-ethyl-1-decene.

In aspects, the $C_{20}$ 2-substituted alpha olefins can additionally include $C_{20}$ 2-substituted alpha olefins selected from the second group of $C_{20}$ 2-substituted alpha olefins: i.e., 2-(4-octyl)-5-propyl-1-nonene, 2-(4-octyl)-6-ethyl-1-decene, 2-(2-ethylhexyl)-5-propyl-1-nonene, 2-(2-ethylhexyl)-6-ethyl-1-decene, or any combination thereof. In one aspect, the $C_{20}$ 2-substituted alpha olefins can further comprise only one, only two, or only three of 2-(4-octyl)-5-propyl-1-nonene, 2-(4-octyl)-6-ethyl-1-decene, 2-(2-ethylhexyl)-5-propyl-1-nonene, and 2-(2-ethylhexyl)-6-ethyl-1-decene. In another aspect, the $C_{20}$ 2-substituted alpha olefins can further comprise 2-(4-octyl)-5-propyl-1-nonene, 2-(4-octyl)-6-ethyl-1-decene, 2-(2-ethylhexyl)-5-propyl-1-nonene, and 2-(2-ethylhexyl)-6-ethyl-1-decene.

In an aspect, the $C_{20}$ 2-substituted alpha olefins can further comprise any amount of 2-(4-octyl)-5-propyl-1-nonene disclosed herein, 2-(4-octyl)-6-ethyl-1-decene disclosed herein, 2-(2-ethylhexyl)-5-propyl-1-nonene disclosed herein, and/or 2-(2-ethylhexyl)-6-ethyl-1-decene disclosed herein. In an aspect, the 2-(4-octyl)-5-propyl-1-nonene, when present, can comprise at least 3, 3.5, or 4 mole % of the $C_{20}$ 2-substituted alpha olefins; alternatively or additionally, a maximum of (less than or equal to) 9, 8.5, 8, 7.5, or 7 mole % of the $C_{20}$ 2-substituted alpha olefins. In another aspect, 2-(4-octyl)-5-propyl-1-nonene, when present, can comprise from any minimum mole % of the $C_{20}$ 2-substituted alpha olefins described herein to any maximum mole % of the $C_{20}$ 2-substituted alpha olefins described herein; for example from 3 mole % to 9 mole %, from 3 mole % to 8.5 mole %, from 3.5 mole % to 8 mole %, from 4 mole % to 7.5 mole %, or from 4 mole % to 7 mole % 2-(4-octyl)-5- propyl-1-nonene. In an aspect, the 2-(4-octyl)-6-ethyl-1-decene, when present, can comprise at least 3, 3.5, or 4 mole % of the $C_{20}$ 2-substituted alpha olefins; alternatively or additionally, a maximum of (less than or equal to) 9, 8, 7, 6.5, or 6 mole % of the $C_{20}$ 2-substituted alpha olefins. In another aspect, 2-(4-octyl)-6-ethyl-1-decene, when present, can comprise from any minimum mole % of the $C_{20}$ 2-substituted alpha olefins described herein to any maximum mole % of the $C_{20}$ 2-substituted alpha olefins described herein; for example from 3 mole % to 9 mole %, from 3 mole % to 8 mole %, from 3.5 mole % to 7 mole %, from 4 mole % to 6.5 mole %, or from 4 mole % to 6 mole % 2-(4-octyl)-6-ethyl-1-decene. In an aspect, the 2-(2-ethylhexyl)-5-propyl-1-nonene, when present, can comprise at least 3, 3.5, or 4 mole % of the $C_{20}$ 2-substituted alpha olefins; alternatively or additionally, a maximum of (less than or equal to) 9, 8, 7, 6.5, or 6 mole % of the $C_{20}$ 2-substituted alpha olefins. In another aspect, 2-(2-ethylhexyl)-5-propyl-1-nonene, when present, can comprise from any minimum mole % of the $C_{20}$ 2-substituted alpha olefins described herein to any maximum mole % of the $C_{20}$ 2-substituted alpha olefins described herein; for example from 3 mole % to 9 mole %, from 3 mole % to 8 mole %, from 3.5 mole % to 7 mole %, from 4 mole % to 6.5 mole %, or from 4 mole % to 6 mole % 2-(2-ethylhexyl)-5-propyl-1-nonene. In an aspect, the 2-(2-ethylhexyl)-6-ethyl-1-decene, when present, can comprise at least 2, 2.5, or 3 mole % of the $C_{20}$ 2-substituted alpha olefins; alternatively or additionally, a maximum of (less than or equal to) 8, 7, 6.5, or 6 mole % of the $C_{20}$ 2-substituted alpha olefins. In another aspect, 2-(2-ethylhexyl)-6-ethyl-1-decene, when present, can comprise from any minimum mole % of the $C_{20}$ 2-substituted alpha olefins described herein to any maximum mole % of the $C_{20}$ 2-substituted alpha olefins described herein; for example from 2 mole % to 8 mole %, from 2 mole % to 7 mole %, from 2.5 mole % to 6.5 mole %, or from 3 mole % to 6 mole % 2-(2-ethylhexyl)-6-ethyl-1-decene.

In aspects, the $C_{20}$ 2-substituted alpha olefins can additionally include $C_{20}$ 2-substituted alpha olefins selected from the third group of $C_{20}$ 2-substituted alpha olefins: i.e., 2-(3-methylheptyl)-1-dodecene, 2-octyl-7-methyl-1-undecene, 2-(4-octyl)-1-dodecene, 2-(3-propylheptyl)-1-decene, 2-(2-ethylhexyl)-1-dodecene, 2-octyl-6-ethyl-1-decene, 2-octyl-1-dodecene, or any combination thereof. In one aspect, the $C_{20}$ 2-substituted alpha olefins can further comprise only one, only two, only three, only four, only five, or only six of 2-(3-methylheptyl)-1-dodecene, 2-octyl-7-methyl-1-undecene, 2-(4-octyl)-1-dodecene, 2-(3-propylheptyl)-1-decene, 2-(2-ethylhexyl)-1-dodecene, 2-octyl-6-ethyl-1-decene, and 2-octyl-1-dodecene. In another aspect, the $C_{20}$ 2-substituted alpha olefins can further comprise 2-(3-methylheptyl)-1-dodecene, 2-octyl-7-methyl-1-undecene, 2-(4-octyl)-1-dodecene, 2-(3-propylheptyl)-1-decene, 2-(2-ethylhexyl)-1-dodecene, 2-octyl-6-ethyl-1-decene, and 2-octyl-1-dodecene.

In an aspect, the $C_{20}$ 2-substituted alpha olefins can further comprise any amount of 2-(3-methylheptyl)-1-dodecene disclosed herein, 2-octyl-7-methyl-1-undecene disclosed herein, 2-(4-octyl)-1-dodecene disclosed herein, 2-(3-propylheptyl)-1-decene disclosed herein, 2-(2-ethylhexyl)-1-dodecene disclosed herein, 2-octyl-6-ethyl-1-decene disclosed herein, and/or 2-octyl-1-dodecene disclosed herein. In an aspect, the 2-(3-methylheptyl)-1-dodecene, when present, can comprise at least 0.5, 1, 1.5, or 2 mole % of the $C_{20}$ 2-substituted alpha olefins; alternatively, or additionally, a maximum of (less than or equal to) 8, 7, 6, 5, or 4 mole % of the $C_{20}$ 2-substituted alpha olefins. In another aspect, 2-(3-methylheptyl)-1-dodecene, when present, can comprise from any minimum mole % of the $C_{20}$ 2-substituted alpha olefins described herein to any maximum mole % of the $C_{20}$ 2-substituted alpha olefins described herein; for example from 0.5 mole % to 8 mole %, from 0.5 mole % to 7 mole %, from 1 mole % to 6 mole %, from 1.5 mole % to 5 mole %, or from 2 mole % to 4 mole % 2-(3-methylheptyl)-1-dodecene. In an aspect, the 2-octyl-7-methyl-1-undecene, when present, can comprise at least 0.5, 1, 1.5, or 2 mole % of the $C_{20}$ 2-substituted alpha olefins; alternatively, or additionally, a maximum of (less than or equal to) 8, 7, 6, 5, or 4 mole % of the $C_{20}$ 2-substituted alpha olefins. In another aspect, 2-octyl-7-methyl-1-undecene, when present, can comprise from any minimum mole % of the $C_{20}$ 2-substituted alpha olefins described herein to any maximum mole % of the $C_{20}$ 2-substituted alpha olefins described herein; for example from 0.5 mole % to 8 mole %, from 0.5 mole % to 7 mole %, from 1 mole % to 6 mole %, from 1.5 mole % to 5 mole %, or from 2 mole % to 4 mole % 2-octyl-7-methyl-1-undecene. In an aspect, the 2-(4-octyl)-1-dodecene, when present, can comprise at least 0.5, 0.75, or 1 mole % of the $C_{20}$ 2-substituted alpha olefins; alternatively, or additionally, a maximum of (less than or equal to) 6, 5, 4, 3, or 2 mole % of the $C_{20}$ 2-substituted alpha olefins. In another aspect, 2-(4-octyl)-1-dodecene, when present, can comprise from any minimum mole % of the $C_{20}$ 2-substituted alpha olefins described herein to any maximum mole % of the $C_{20}$ 2-substituted alpha olefins described herein; for example from 0.5 mole % to 6 mole %, from 0.5 mole % to 5 mole %, from 0.75 mole % to 4 mole %, from 0.75 mole % to 3 mole %, or from 1 mole % to 2 mole % 2-(4-octyl)-1-dodecene. In an aspect, the 2-(3-propylheptyl)-1-decene, when present, can comprise at least 0.5, 0.75, or 1 mole % of the $C_{20}$ 2-substituted alpha olefins; alternatively, or additionally, a maximum of (less than or equal to) 6, 5, 4, 3, or 2 mole % of the $C_{20}$ 2-substituted alpha olefins. In another aspect, 2-(3-propylheptyl)-1-decene, when present, can comprise from any minimum mole % of the $C_{20}$ 2-substituted alpha olefins described herein to any maximum mole % of the $C_{20}$ 2-substituted alpha olefins described herein; for example from 0.5 mole % to 6 mole %, from 0.5 mole % to 5 mole %, from 0.75 mole % to 4 mole %, from 0.75 mole % to 3 mole %, or from 1 mole % to 2 mole % 2-(3-propylheptyl)-1-decene. In an aspect, the 2-(2-ethylhexyl)-1-dodecene, when present, can comprise at least 0.5, 0.75, or 1 mole % of the $C_{20}$ 2-substituted alpha olefins; alternatively, or additionally, a maximum of (less than or equal to) 6, 5, 4, 3, or 2 mole % of the $C_{20}$ 2-substituted alpha olefins. In another aspect, 2-(2-ethylhexyl)-1-dodecene, when present, can comprise from any minimum mole % of the $C_{20}$ 2-substituted alpha olefins described herein to any maximum mole % of the $C_{20}$ 2-substituted alpha olefins described herein; for example from 0.5 mole % to 6 mole %, from 0.5 mole % to 5 mole %, from 0.75 mole % to 4 mole %, from 0.75 mole % to 3 mole %, or from 1 mole % to 2 mole % 2-(2-ethylhexyl)-1-dodecene. In an aspect, the 2-octyl-6-ethyl-1-decene, when present, can comprise at least 0.5, 0.75, or 1 mole % of the $C_{20}$ 2-substituted alpha olefins; alternatively, or additionally, a maximum of (less than or equal to) 6, 5, 4, 3, or 2 mole % of the $C_{20}$ 2-substituted alpha olefins. In another aspect, 2-octyl-6-ethyl-1-decene, when present, can comprise from any minimum mole % of the $C_{20}$ 2-substituted alpha olefins described herein to any maximum mole % of the $C_{20}$ 2-substituted alpha olefins described herein; for example from 0.5 mole % to 6 mole %, from 0.5 mole % to 5 mole %, from 0.75 mole % to 4 mole %, from 0.75 mole % to 3 mole %, or from 1 mole % to 2 mole % 2-octyl-6-ethyl-1-decene. In an aspect, the 2-octyl-1-dodecene, when present, can comprise at least 0.1, 0.15, or 0.2 mole % of the $C_{20}$ 2-substituted alpha olefins; alternatively, or additionally, a maximum of (less than or equal to) 5, 4, 3, 2, or 1 mole % of the $C_{20}$ 2-substituted alpha olefins. In another aspect, 2-octyl-1-dodecene, when present, can comprise from any minimum mole % of the $C_{20}$ 2-substituted alpha olefins described herein to any maximum mole % of the $C_{20}$ 2-substituted alpha olefins described herein; for example from 0.1 mole % to 5 mole %, from 0.1 mole % to 4 mole %, from 0.15 mole % to 3 mole %, from 0.15 mole % to 2 mole %, or from 0.2 mole % to 1 mole % 2-octyl-1-dodecene.

In an aspect, a process can comprise 1) contacting i) a $C_{10}$ olefin composition comprising branched $C_{10}$ olefins (or branched $C_{10}$ alpha olefins) and ii) a dimerization catalyst or dimerization catalyst system and; 2) forming a reaction product comprising $C_{20}$ 2-substituted alpha olefins. In another aspect, a process can comprise 1) contacting i) a $C_{10}$ olefin composition comprising branched $C_{10}$ olefins (or branched $C_{10}$ alpha olefins), the branched $C_{10}$ olefins comprising 3-propyl-1-heptene, 4-ethyl-1-octene, 5-methyl-1-nonene or any combination thereof, and ii) a dimerization catalyst or dimerization catalyst system; 2) forming a reaction product comprising $C_{20}$ 2-substituted alpha olefins, where the $C_{20}$ 2-substituted alpha olefins comprise 2-(3-methylheptyl)-7-methyl-1-undecene, 2-(4-octyl)-7-methyl-1-undecene, 2-(3-methylheptyl)-5-propyl-1-nonene, 2-(2-ethylhexyl)-7-methyl-1-undecene, 2-(3-methylheptyl)-6-ethyl-1-decene, or any combination thereof. In yet another aspect, a process can comprise 1) contacting i) a $C_{10}$ olefin composition comprising branched $C_{10}$ olefins (or branched $C_{10}$ alpha olefins), the branched $C_{10}$ olefins comprising 3-propyl-1-heptene, 4-ethyl-1-octene, 5-methyl-1-nonene or any combination thereof, and ii) a dimerization catalyst or dimerization catalyst system; 2) forming a reaction product comprising $C_{20}$ 2-substituted alpha olefins, where the $C_{20}$ 2-substituted alpha olefins comprise 2-(3-methylheptyl)-7-methyl-1-undecene, 2-(4-octyl)-7-methyl-1-undecene, 2-(3-methylheptyl)-5-propyl-1-nonene, 2-(2-ethylhexyl)-7-methyl-1-undecene, and 2-(3-methylheptyl)-6-ethyl-1-decene. In an aspect, the reaction product can comprise at least 50 mole % $C_{20}$ 2-substituted alpha olefins (or any other mole % $C_{20}$ 2-substituted alpha olefins disclosed herein). In other aspects, the reaction product can further comprise $C_{20}$ 2-substituted alpha olefins from the second and/or third group of $C_{20}$ 2-substituted alpha olefins as described herein. The conditions capable of forming a reaction product are described herein and can be utilized without limitation to further describe the processes described herein. In an aspect, the reaction product comprising $C_{20}$ 2-substituted alpha olefins can be formed in a reaction zone. In some aspects, the reaction product can be formed under conditions capable of forming a reaction product comprising $C_{20}$ 2-substituted alpha olefins. In other aspects, the reaction product can further comprise $C_{20}$ 2-substituted alpha olefins from the second and/or third group of $C_{20}$ 2-substituted alpha olefins as described herein. The conditions capable of forming a reaction product are described herein and can be utilized without limitation to further describe the processes described herein.

The reaction zone (or dimerization reaction zone) can comprise a reactor (or dimerization reactor) and optionally any equipment (e.g., pumps, compressors, valves, and piping) where the reaction conditions necessary to form a reaction product (or dimerization reaction product) are present. The process can operate as a batch process or as a continuous process and/or operate with or without recycle. Additionally, the process can utilize one or more reaction zones. Each reaction zone (or dimerization reaction zone) of the one or more reaction zones can comprise one or more reactors (or dimerization reactors). In an aspect, each reactor independently can be a stirred tank reactor, a continuous-stirred tank reactor, a fixed bed reactor, or a plug flow reactor.

In aspects, the disclosed processes can include additional steps which can occur before contacting the branched $C_{10}$ olefins (or branched $C_{10}$ alpha olefins) and the dimerization catalyst or dimerization catalyst system. Additional steps that can occur before contacting the branched $C_{10}$ olefins and the dimerization catalyst or dimerization catalyst system can include separating (or removing) impurities from the $C_{10}$ olefin composition. For example, the $C_{10}$ olefin composition can contain heteroatomic compounds in addition to desirable branched $C_{10}$ olefins (or branched $C_{10}$ alpha olefins). The heteroatomic compounds, for example, amines (e.g., pyrroles, among others), peroxides, and alcohols (e.g., ethyl hexanol), may be present in the $C_{10}$ olefin composition as isolated from the composition from which the $C_{10}$ olefin composition is obtained. Thus, in an aspect the processes can include forming the $C_{10}$ olefin composition that is substantially devoid of heteroatomic compounds. For example, the processes can further comprise removing heteroatomic compounds from the $C_{10}$ olefin composition by distillation and/or contacting the $C_{10}$ olefin composition with an adsorbent; alternatively, distillation; or alternatively, contacting the $C_{10}$ olefin composition with an adsorbent. In an aspect, the adsorbent can comprise, can consist essentially of, or can be a silica, an alumina, a molecular sieve, a clay, a charcoal, a titania, a magnesia, a zirconia, an aluminosilicate, a zeolite, diatomaceous earth, or any combination thereof; alternatively, a silica, an alumina, a molecular sieve, a charcoal, an aluminosilicate, a zeolite, or any combination thereof; alternatively, a silica, an alumina, a molecular sieve, a charcoal; alternatively, a silica; alternatively, an alumina; alternatively, a molecular sieve; or alternatively, a charcoal.

Additional steps that can occur after contacting the branched $C_{10}$ olefins and the dimerization catalyst or catalyst system can include recovering the dimerization product. In aspects, recovering the dimerization product can include recovering an effluent containing the dimerization product from the dimerization reactor system.

Additional steps can occur after formation of the reaction product (or dimerization reaction product). In an aspect, the processes described herein can further comprise discharging a reaction zone effluent (or a dimerization reaction zone effluent). In an aspect, the processes can further comprise separating the dimerization catalyst or dimerization catalyst system from the reaction zone effluent (or dimerization reaction zone effluent). In an aspect, the processes described herein can further comprise deactivating the dimerization catalyst or dimerization catalyst system to form a deactivated reaction zone effluent (or deactivated dimerization reaction zone effluent). In other aspects, the processes described herein can further comprise deactivating the dimerization catalyst or dimerization catalyst system to form a deactivated reaction zone effluent (or deactivated dimerization reaction zone effluent) and the separating the deactivated dimerization catalyst or dimerization catalyst system (or deactivated dimerization catalyst or deactivated dimerization catalyst system) from the deactivated reaction zone effluent (or deactivated dimerization reaction zone effluent). In an aspect, the processes can further comprise separating the dimerization catalyst or dimerization catalyst system from the reaction zone effluent (or dimerization reaction zone effluent) or separating the deactivated dimerization catalyst or deactivated dimerization catalyst system from the deactivated reaction zone effluent (or deactivate dimerization reaction zone effluent) by filtration or distillation; alternatively, filtration; or alternatively distillation. In an aspect, the processes can include isolating a composition comprising $C_{20}$ 2-substituted alpha olefins from the reaction zone effluent (or a dimerization reaction zone effluent) or deactivated reaction zone effluent (or the deactivated dimerization reaction zone effluent). In an aspect, the processes can further comprise separating the unconverted branched $C_{10}$ olefins from the reaction zone effluent (or dimerization reaction zone effluent) or separating the deactivated dimerization catalyst or deactivated dimerization catalyst system from the deactivated reaction zone effluent (or deactivated dimerization reaction zone effluent). In an aspect, reaction zone effluent (or dimerization reaction zone effluent) or the deactivated reaction zone effluent (or deactivated dimerization reaction zone effluent) can be distilled in a distillation column (e.g., before or after catalyst (or catalyst system) or deactivated catalyst (or deactivated catalyst system) removal) to isolate a composition comprising the $C_{20}$ 2-substituted alpha olefins. In some aspects, the unconverted branched $C_{10}$ olefins can be recovered as an overhead product line from the distillation column and the $C_{20}$ 2-substituted alpha olefins can be recovered as a bottom product from the distillation column. In aspects where distillation is performed before catalyst (or deactivated catalyst) of catalyst system (or deactivated catalyst system) removal, the bottom product line of the distillation column can also contain the catalyst (or deactivated catalyst) of catalyst system (or deactivated catalyst system). In an aspect, the catalyst (or deactivated catalyst) of catalyst system (or deactivated catalyst system) can be removed from the bottom product by filtration. In aspects, the processes described herein can isolate a composition comprising the $C_{20}$ 2-substituted alpha olefins that can be substantially devoid of catalyst (or deactivated catalyst). "Substantially devoid of catalyst" (or "substantially devoid of deactivated catalyst") as used herein means a concentration of catalyst or deactivated catalyst which is less than 1, 0.1, 0.01, 0.001, or 0.0001 mass % based on a total mass of the composition comprising the $C_{20}$ 2-substituted alpha olefins.

Any suitable dimerization conditions for the disclosed process can be employed, as would be recognized by those skilled in the art in view of this disclosure, in U.S. Pat. Nos. 2,695,327; 4,658,078; 4,973,788; 5,087,788; 5,625,105; and 6,756,514, and U.S. Patent Application Publication No. 2019/0062234.

Generally, the pressure which can be utilized to form the reaction product can be any pressure capable of forming the reaction product. In an aspect, the minimum pressure which can be utilized for forming the reaction product can be 10 psia (69 kPa), or 14.0 psia (97 kPa), 14.7 psia (101 kPa), or 20 psia (138); alternatively or additionally, the maximum pressure which can be utilized for forming the reaction product can be 1,000 psia (6.9 MPa), 500 psia (3.4 MPa), 400 psia (2.8 MPa), 300 psia (2 MPa), 200 psia (1.4 MPa), or 100 psia (689 kPa). Ranges of pressure which can be utilized for forming the reaction product can range from any minimum pressure described herein to any maximum pressure described herein. In some aspects, suitable ranges for the pressure which can be utilized to form the reaction product can include, but are not limited to, from 10 psia (69 kPa) to 1,000 psia (6.9 MPa), from 10 psia (69 kPa) to 500 psia (3.4 MPa), from 14 psia (97 kPa) to 400 psia (2.8 MPa), from 14 psia (97 kPa) to 300 psia (3.4 MPa), from 14.7 psia (101 kPa) to 200 psia (1.4 MPa), or from 14.7 psia (101 kPa) to 100 psia (689 KPa). Other ranges of pressure for forming the reaction product are readily apparent to those skilled in the art with the aid of this disclosure.

Generally, the temperature which can be utilized to form the reaction product can be any temperature capable of forming the reaction product. In an aspect, the minimum temperature which can be utilized for forming the reaction product can be −60° C., −30° C., 0° C., 20° C., 50° C., 75° C., or 100° C.; alternatively or additionally, the maximum temperature which can be utilized for forming the reaction product can be 280° C., 250° C., 230° C., 200° C., 175° C., 150° C., or 125° C. Ranges of temperature which can be utilized which can be utilized for forming the reaction product can range from any minimum temperature to any maximum temperature described herein for dimerization conditions. In some aspects, suitable ranges for the temperature which can be utilized as dimerization conditions be include, but are not limited to, from −60° C. to 280° C.; alternatively, from −30 C to 250° C.; alternatively, from 0° C. to 230° C.; alternatively, from 100° C. to 250° C.; alternatively, from 100° C. to 230° C.; alternatively, from 100° C. to 200° C.; alternatively, from 0° C. to 150° C.; alternatively, from 0° C. to 125° C.; or alternatively, from 20° C. to 100° C. Other ranges of temperature for forming the reaction product are readily apparent to those skilled in the art with the aid of this disclosure.

In an aspect, the conditions for forming the reaction product can include a reaction time in the reactor zone and is generally any time that can produce the desired quantity of dimerization product; alternatively, any time that can provide a desired dimerization catalyst or catalyst system productivity; alternatively, any time that can provide a desired conversion of a $C_{10}$ olefin composition disclosed herein (e.g., a conversion of at least 50 wt. %; alternatively, at least 60 wt. %; alternatively, at least 70 wt. %; alternatively, at least 80 wt. %). The minimum time (or minimum average time) can be 1 minute, 10 minutes, 30 minutes, 45 minutes, or 1 hour; alternatively or additionally, the maximum time (or average maximum time) can be 48 hours, 36 hours, 24 hours, 12 hours, 6 hours, 4 hours, or 2 hours. Ranges of reaction time which can be utilized for forming the reaction product can range from any minimum time described herein to any maximum time described herein. In some aspects, suitable ranges for the reaction time which can be utilized as dimerization conditions be include, but are not limited to, from 1 minute to 48 hours, from 10 minutes to 36 hours, from 30 minutes to 24 hours, from 45 minutes to 24 hours, from 1 hour to 12 hours, from 1 hour to 6 hours or from 1 hour to 2 hours. Other time ranges for forming the reaction product are readily apparent to those skilled in the art with the aid of this disclosure.

In additional aspects, the dimerization conditions can include reaction under an inert atmosphere, such as under a nitrogen blanket.

EXAMPLES

The following examples illustrate various aspects of the $C_{10}$ olefin composition and $C_{20}$ products obtained by dimerization reaction thereof.

Example 1

Example 1 demonstrates exemplary $C_{10}$ olefin compositions for use in dimerization reactions to produce the $C_{20}$ 2-substituted alpha olefin disclosed herein. Feedstock $C_{10}$ olefin compositions comprising branched $C_{10}$ olefins (or branched $C_{10}$ alpha olefins) were obtained by taking samples of a by-product $C_{10}$ olefin stream from a commercial plant employing selective ethylene trimerization to 1-hexene technology. Dimethyl pyrrole and other heteroatomic compounds contained in the sample were removed from the sample by contact with silica gel to produce the feedstock $C_{10}$ olefin compositions comprising branched $C_{10}$ olefins (or branched $C_{10}$ alpha olefins). The concentration of each component of the feedstock $C_{10}$ olefin compositions is reported as an average in the samples, a minimum in the samples, and a maximum in the samples is provided in Table 1 below:

TABLE 1

| Component | Average (mass %) | Minimum (mass %) | Maximum (mass %) |
| --- | --- | --- | --- |
| 1-decene | 4.8 | 3.6 | 6.0 |
| 2-butyl-1-hexene | 11.8 | 8.9 | 14.8 |
| 3-propyl-1-heptene | 17.4 | 13.1 | 21.8 |
| 4-ethyl-1-octene | 15.6 | 11.7 | 19.5 |
| 5-methyl-1-nonene | 38.2 | 28.7 | 47.8 |
| 4/5-decenes | 10.8 | 8.1 | 13.5 |

Example 2

The average values of the $C_{10}$ olefin compositions comprising branched $C_{10}$ olefins (or branched $C_{10}$ alpha olefins) identified in Table 1 were entered into a proprietary dimerization reaction simulator, developed by Chevron Phillips Chemical Company LP. The dimerization simulation produced the results for the $C_{20}$ 2-substituted alpha olefins as provided in Table 2.

TABLE 2

| Product | Mass % |
| --- | --- |
| 2-(3-methylheptyl)-7-methyl-1-undecene | 25.2 |
| 2-(4-octyl)-7-methyl-1-undecene | 11.5 |
| 2-(3-methylheptyl)-5-propyl-1-nonene | 11.5 |
| 2-(2-ethylhexyl)-7-methyl-1-undecene | 10.3 |
| 2-(3-methylheptyl)-6-ethyl-1-decene | 10.3 |
| 2-(4-octyl)-5-propyl-1-nonene | 5.2 |
| 2-(4-octyl)-6-ethyl-1-decene | 4.7 |
| 2-(2-ethylhexyl)-5-propyl-1-nonene | 4.7 |
| 2-(2-ethylhexyl)-6-ethyl-1-decene | 4.2 |
| 2-(3-methylheptyl)-1-dodecene | 3.2 |
| 2-octyl-7-methyl-1-undecene | 3.2 |
| 2-(4-octyl)-1-dodecene | 1.5 |
| 2-(3-propylheptyl)-1-decene | 1.5 |
| 2-(2-ethylhexyl)-1-dodecene | 1.3 |
| 2-octyl-6-ethyl-1-decene | 1.3 |
| 2-octyl-1-dodecene | 0.4 |

As can be seen, 25.2 mass % of the product was attributable to 2-(3-methylheptyl)-7-methyl-1-undecene. About 43.6 mass % was attributable to four $C_{20}$ 2-substituted alpha olefins: 2-(4-octyl)-7-methyl-1-undecene, 2-(3-methylheptyl)-5-propyl-1-nonene, 2-(2-ethylhexyl)-7-methyl-1-undecene, and 2-(3-methylheptyl)-6-ethyl-1-decene. Smaller amount for each of 2-(4-octyl)-5-propyl-1-nonene, 2-(4-octyl)-6-ethyl-1-decene, 2-(2-ethylhexyl)-5-propyl-1-nonene, 2-(2-ethylhexyl)-6-ethyl-1-decene, 2-(3-methylheptyl)-1-dodecene, 2-octyl-7-methyl-1-undecene, 2-(4-octyl)-1-dodecene, 2-(3-propylheptyl)-1-decene, 2-(2-ethylhexyl)-1-dodecene, 2-octyl-6-ethyl-1-decene, and 2-octyl-1-dodecene (ranging from 5.2 mass % down to 0.4 mass %) made the balance of the reaction product.

Example 3

The dimerization reaction simulator was again used to determine a potential concentration range for the $C_{20}$ 2-substituted alpha olefins based on the minimum and maximum values of the $C_{10}$ olefin compositions comprising branched $C_{10}$ olefins (or branched $C_{10}$ alpha olefins) identified in Table 1. The dimerization simulation produced the results for the $C_{20}$ 2-substituted alpha olefins as provided in Table 3:

TABLE 3

| Product | Mass % |
| --- | --- |
| 2-(3-methylheptyl)-7-methyl-1-undecene | 21-29 |
| 2-(4-octyl)-7-methyl-1-undecene | 10-13 |
| 2-(3-methylheptyl)-5-propyl-1-nonene | 10-13 |
| 2-(2-ethylhexyl)-7-methyl-1-undecene | 9-12 |
| 2-(3-methylheptyl)-6-ethyl-1-decene | 9-12 |
| 2-(4-octyl)-5-propyl-1-nonene | 4-7 |
| 2-(4-octyl)-6-ethyl-1-decene | 4-6 |
| 2-(2-ethylhexyl)-5-propyl-1-nonene | 4-6 |
| 2-(2-ethylhexyl)-6-ethyl-1-decene | 3-6 |
| 2-(3-methylheptyl)-1-dodecene | 2-4 |
| 2-octyl-7-methyl-1-undecene | 2-4 |
| 2-(4-octyl)-1-dodecene | 1-2 |
| 2-(3-propylheptyl)-1-decene | 1-2 |
| 2-(2-ethylhexyl)-1-dodecene | 1-2 |
| 2-octyl-6-ethyl-1-decene | 1-2 |
| 2-octyl-1-dodecene | 0-1 |

As can be seen, the largest amount of $C_{20}$ 2-substituted alpha olefins in the product was attributable to 2-(3-methylheptyl)-7-methyl-1-undecene, in a range of 21 to 29 mass %. About 38-50 mass % of the product was attributable to four $C_{20}$ 2-substituted alpha olefins: 2-(4-octyl)-7-methyl-1-undecene, 2-(3-methylheptyl)-5-propyl-1-nonene, 2-(2-ethylhexyl)-7-methyl-1-undecene, and 2-(3-methylheptyl)-6-ethyl-1-decene. Smaller ranges for each of 2-(4-octyl)-5-propyl-1-nonene, 2-(4-octyl)-6-ethyl-1-decene, 2-(2-ethylhexyl)-5-propyl-1-nonene, 2-(2-ethylhexyl)-6-ethyl-1-decene, 2-(3-methylheptyl)-1-dodecene, 2-octyl-7-methyl-1-undecene, 2-(4-octyl)-1-dodecene, 2-(3-propylheptyl)-1-decene, 2-(2-ethylhexyl)-1-dodecene, 2-octyl-6-ethyl-1-decene, and 2-octyl-1-dodecene made the balance of the reaction product.

Example 4

A sample of a $C_{10}$ olefin composition having a $C_{10}$ distribution corresponding to the average distribution provided in Table 1 was treated with silica gel to remove polar species. The treated $C_{10}$ olefin composition, 500 grams, was combined with triethylaluminum, 5 grams, under nitrogen. The mixture was heated to 200° C. for six hours with stirring. After six hours, the reaction mixture was cooled and then washed with aqueous NaOH to remove catalyst residues. The organic and aqueous phases were separated. About 50 mass % of the organic mixture consisted of $C_{20}$ olefins, which were isolated by vacuum distillation. GC/FID analysis of the isolated organic product provided a chromatogram, illustrated in the FIGURE, for the $C_{20}$ region the isolated organic product. The number and relative peak areas are consistent with the product mixture predicted from the dimer simulation provided in Table 3. The GC/FID chromatogram of the $C_{20}$ region, illustrated in the FIGURE, showed five major peaks (peaks labeled 1, 2, 3, 4, and 5) having relative peak areas consistent with the predicted major dimer product of Example 3: i.e., 2-(3-methylheptyl)-7-methyl-1-undecene (peak 1), 2-(4-octyl)-7-methyl-1-undecene (peak 2), 2-(3-methylheptyl)-5-propyl-1-nonene (peak 3), 2-(2-ethylhexyl)-7-methyl-1-undecene (peak 4), and 2-(3-methylheptyl)-6-ethyl-1-decene (peak 5). The GC/FID analysis also showed other $C_{20}$ isomers consistent with the predicted dimer product of Example 3.

ADDITIONAL DISCLOSURE

The following is provided as additional disclosure for combinations of features and aspects of the present invention.

Statement 1. A composition comprising $C_{20}$ 2-substituted alpha olefins, wherein the $C_{20}$ 2-substituted alpha olefins comprise 2-(3-methylheptyl)-7-methyl-1-undecene, 2-(4-octyl)-7-methyl-1-undecene, 2-(3-methylheptyl)-5-propyl-1-nonene, 2-(2-ethylhexyl)-7-methyl-1-undecene, 2-(3-methylheptyl)-6-ethyl-1-decene, or any combination thereof.

Statement 2. A process comprising: 1) contacting i) a $C_{10}$ olefin composition comprising branched $C_{10}$ olefins, the branched $C_{10}$ olefins comprising 3-propyl-1-heptene, 4-ethyl-1-octene, 5-methyl-1-nonene or any combination thereof, and ii) a dimerization catalyst or dimerization catalyst system; 2) forming a reaction product comprising $C_{20}$ 2-substituted alpha olefins; and 3) isolating a composition comprising $C_{20}$ 2-substituted alpha olefins, wherein the $C_{20}$ 2-substituted alpha olefins comprise 2-(3-methylheptyl)-7-methyl-1-undecene, 2-(4-octyl)-7-methyl-1-undecene, 2-(3-methylheptyl)-5-propyl-1-nonene, 2-(2-ethylhexyl)-7-methyl-1-undecene, 2-(3-methylheptyl)-6-ethyl-1-decene, or any combination thereof.

Statement 3. The process defined in statement 3, wherein the $C_{10}$ olefin composition comprising branched $C_{10}$ olefins comprises any minimum or range of branched $C_{10}$ olefins disclosed herein (e.g., at least 50 mole % branched $C_{10}$ olefins or from 50 mole % to 99.5 mole % branched $C_{10}$ olefins, among others disclosed herein).

Statement 4. The process defined in statement 2 or 3, wherein the branched $C_{10}$ olefins comprises 3-propyl-1-heptene, 4-ethyl-1-octene, 5-methyl-1-nonene, or any combination thereof.

Statement 5. The process defined in statement 2 or 3, wherein the branched $C_{10}$ olefins comprises 3-propyl-1-heptene, 4-ethyl-1-octene, and 5-methyl-1-nonene.

Statement 6. The process defined in any one of statements 2-5, wherein the branched $C_{10}$ olefins comprise any minimum or range of 3-propyl-1-heptene, 4-ethyl-1-octene, and/or 5-methyl-1-nonene disclosed herein (e.g., i) at least 8 mole % 3-propyl-1-heptene, ii) at least 6 mole % 4-ethyl-1-octene, and iii) at least 20 mole % 5-methyl-1-nonene, or i) from 8 mole % to 35 mole % 3-propyl-1-heptene, ii) from 6 mole % to 30 mole % 4-ethyl-1-octene, and iii) from 20 mole % to 65 mole % 5-methyl-1-nonene, among others disclosed herein).

Statement 7. The process defined in any one of statements 2-6, wherein the branched $C_{10}$ olefins further comprise 2-butyl-1-hexene.

Statement 8. The process defined in statement 7, wherein the branched $C_{10}$ olefins comprise any minimum or range of 2-butyl-1-hexene disclosed herein (e.g., at least 3 mole % 2-butyl-1-hexene or from 3 mole % to 25 mole % 2-butyl-1-hexene, among others disclosed herein.

Statement 9. The process of any one of statements 2-8, wherein the $C_{10}$ olefin composition comprises linear $C_{10}$ olefins.

Statement 10. The process defined in statement 9, wherein the linear $C_{10}$ olefins comprise any maximum or range of linear $C_{10}$ olefins disclosed herein (e.g., a maximum of 50 mole % linear $C_{10}$ olefins or from 0 mole % to 50 mole % linear $C_{10}$ olefins, among others disclosed herein).

Statement 11. The process defined in statement 9, wherein the linear $C_{10}$ olefins comprise i) 1-decene, ii) 4- and/or 5-decene, or iii) any combination of i) and ii).

Statement 12. The process defined in statement 11, wherein the linear $C_{10}$ olefins comprise any maximum or range of 1-decene disclosed herein (e.g., a maximum of 40 mole % 1-decene or from 0 mole % to 40 mole % 1-decene, among others disclosed herein).

Statement 13. The process defined in statement 11 or 12, wherein the linear $C_{10}$ olefins comprise any maximum or range of 4- and/or 5-decene disclosed herein (e.g., a maximum of 25 mole % linear $C_{10}$ olefins or from 0 mole % to 25 mole % linear $C_{10}$ olefins, among others disclosed herein).

Statement 14. The process defined in any one of statements 2-13, wherein the dimerization catalyst or dimerization catalyst system comprises i) an alkylaluminum compound, ii) a zirconium compound, or iii) a metallocene compound.

Statement 15. The process defined in statement 14, wherein the dimerization catalyst comprise (or is) the alkylaluminum compound and the alkylaluminum compound consists essentially of a trialkylaluminum compound.

Statement 16. The process defined in statement 14, wherein the dimerization catalyst system comprises (or is) the zirconium compound and an aluminoxane, wherein the zirconium compound comprises zirconium dichloride.

Statement 17. The process defined in statement 14, wherein the dimerization catalyst system comprises (or is) the metallocene compound and (a) an aluminoxane or (b) a non-coordinating anion and an alkylaluminum compound.

Statement 18. The process defined in any one of statements 2-17, wherein the $C_{10}$ olefin composition is a $C_{10}$ olefin composition substantially devoid of heteroatomic compounds.

Statement 19. The process defined in statement 18, wherein the process further comprises forming the $C_{10}$ olefin composition substantially devoid of heteroatomic compounds by removing a heteroatomic compound from the $C_{10}$ olefin composition.

Statement 20. The process defined in any one of statements 2-19, wherein isolating the composition comprising $C_{20}$ 2-substituted alpha olefins comprises distilling the dimerization product.

Statement 21. The composition defined in statement 1, or the process defined in any one of statements 2-20, wherein the $C_{20}$ 2-substituted alpha olefins comprise any minimum of $C_{20}$ 2-substituted alpha olefins disclosed herein (e.g., at least 50 mole %, at least 60 mole %, at least 70 mole %, at least 75 mole %, at least 80 mole %, at least 85 mole %, at least 90 mole %, or at least 95 mole % $C_{20}$ 2-substituted alpha olefins).

Statement 22. The composition defined in statement 1 or 21, or the process defined in any one of statements 2-21, wherein the $C_{20}$ 2-substituted alpha olefins comprise 2-(3-methylheptyl)-7-methyl-1-undecene, 2-(4-octyl)-7-methyl-1-undecene, 2-(3-methylheptyl)-5-propyl-1-nonene, 2-(2-ethylhexyl)-7-methyl-1-undecene, and 2-(3-methylheptyl)-6-ethyl-1-decene.

Statement 23. The composition or process defined in statement 22, wherein the $C_{20}$ 2-substituted alpha olefins comprise any minimum or range of 2-(3-methylheptyl)-7-methyl-1-undecene, 2-(4-octyl)-7-methyl-1-undecene, 2-(3-methylheptyl)-5-propyl-1-nonene, 2-(2-ethylhexyl)-7-methyl-1-undecene, and/or 2-(3-methylheptyl)-6-ethyl-1-decene disclosed herein (e.g., at least 10 mole % 2-(3-methylheptyl)-7-methyl-1-undecene, at least 5 mole % 2-(4-octyl)-7-methyl-1-undecene, at least 5 mole % 2-(3-methylheptyl)-5-propyl-1-nonene, at least 5 mole % 2-(2-ethylhexyl)-7-methyl-1-undecene, and/or at least 5 mole % 2-(3-methylheptyl)-6-ethyl-1-decene; or from 20 mole % to 30 mole % 2-(3-methylheptyl)-7-methyl-1-undecene, from 7 mole % to 15 mole % 2-(4-octyl)-7-methyl-1-undecene, from 7 mole % to 15 mole % 2-(3-methylheptyl)-5-propyl-1-nonene, from 7 mole % to 15 mole % 2-(2-ethylhexyl)-7-methyl-1-undecene, and/or from 7 mole % to 15 mole % 2-(3-methylheptyl)-6-ethyl-1-decene; among others disclosed herein).

Statement 24. The composition defined in any one of statements 1 or 21-23, or the process defined in any one of statements 2-23, wherein the $C_{20}$ 2-substituted alpha olefins further comprise 2-(4-octyl)-5-propyl-1-nonene, 2-(4-octyl)-6-ethyl-1-decene, 2-(2-ethylhexyl)-5-propyl-1-nonene, 2-(2-ethylhexyl)-6-ethyl-1-decene, or any combination thereof.

Statement 25. The composition or process defined in statement 24, wherein the $C_{20}$ 2-substituted alpha olefins comprise any minimum or range of 2-(4-octyl)-5-propyl-1-nonene, 2-(4-octyl)-6-ethyl-1-decene, 2-(2-ethylhexyl)-5-propyl-1-nonene, and/or 2-(2-ethylhexyl)-6-ethyl-1-decene (e.g., at least 3 mole % 2-(4-octyl)-5-propyl-1-nonene, at least 3 mole % 2-(4-octyl)-6-ethyl-1-decene, at least 3 mole % 2-(2-ethylhexyl)-5-propyl-1-nonene, and/or at least 2.5 mole % 2-(2-ethylhexyl)-6-ethyl-1-decene; or from 3 mole % to 9 mole % 2-(4-octyl)-5-propyl-1-nonene, from 3 mole % to 9 mole % 2-(4-octyl)-6-ethyl-1-decene, from 3 mole % to 9 mole % 2-(2-ethylhexyl)-5-propyl-1-nonene, and/or from 2 mole % to 8 mole % 2-(2-ethylhexyl)-6-ethyl-1-decene; among others disclosed herein).

Statement 26. The composition defined in any one of statements 1 or 21-25, or the process defined in any one of statements 2-25, wherein the $C_{20}$ 2-substituted alpha olefins further comprises 2-(3-methylheptyl)-1-dodecene, 2-octyl-7-methyl-1-undecene, 2-(4-octyl)-1-dodecene, 2-(3-propylheptyl)-1-decene, 2-(2-ethylhexyl)-1-dodecene, 2-octyl-6-ethyl-1-decene, 2-octyl-1-dodecene, or any combination thereof.

Statement 27. The composition or process defined in statement 26, wherein the $C_{20}$ 2-substituted alpha olefins comprise any minimum or range of 2-(3-methylheptyl)-1-dodecene, 2-octyl-7-methyl-1-undecene, 2-(4-octyl)-1-dodecene, 2-(3-propylheptyl)-1-decene, 2-(2-ethylhexyl)-1-dodecene, 2-octyl-6-ethyl-1-decene, and/or 2-octyl-1-dodecene disclosed herein (e.g., at least 0.5 mole % of 2-(3-methylheptyl)-1-dodecene, at least 0.5 mole % of 2-octyl-7-methyl-1-undecene, at least 0.5 mole % of 2-(4-octyl)-1-dodecene, at least 0.5 mole % of 2-(3-propylheptyl)-1-decene, at least 0.5 mole % of 2-(2-ethylhexyl)-1-dodecene, at least 0.5 mole % of 2-octyl-6-ethyl-1-decene, and at least 0.1 mole % of 2-octyl-1-dodecene; or from 0.5 mole % to 8 mole % 2-(3-methylheptyl)-1-dodecene, from 0.5 mole % to 8 mole % 2-octyl-7-methyl-1-undecene, 0.5 mole % to 6 mole % 2-(4-octyl)-1-dodecene, 0.5 mole % to 6 mole % 2-(3-propylheptyl)-1-decene, 0.5 mole % to 6 mole % 2-(2-ethylhexyl)-1-dodecene, from 0.5 mole % to 6 mole % 2-octyl-6-ethyl-1-decene, from 0.1 mole % to 5 mole % 2-octyl-1-dodecene; among others disclosed herein).

Statement 28. The composition defined in any one of statements 1 or 21-27, or the process defined in any one of statements 2-27, wherein the composition is an additive for a lube oil.

Statement 29. The process defined in any one of statements 2-27, further comprising adding the composition to a lube oil.

Statement 30. A lube oil comprising the composition defined in any one of statements 1 or 21-28.

Statement 31. A feedstock for making a paper sizing agent comprising the composition defined in any one of statements 1 or 24-27.

Statement 32. The process defined in any one of statements 2-27, further comprising reacting the composition with maleic anhydride to form a $C_{20}$ alkenyl succinic anhydride.

While statements of the disclosure have been shown and described, modifications thereof can be made without departing from the spirit and teachings of the invention. The statements and examples described herein are exemplary only, and are not intended to be limiting. Many variations and modifications of the invention disclosed herein are possible and are within the scope of the invention.

At least one aspect is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, 5, 6, . . . ; greater than 0.10 includes 0.11, 0.12, 0.13, 0.14, 0.15, . . . ). For example, whenever a numerical range with a lower limit, $R_l$, and an upper limit, $R_u$, is disclosed, any number falling within the range is specifically disclosed. In particular, the following numbers within the range are specifically disclosed: $R=R_l+k^* (R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, % percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an aspect of the present invention. Thus, the claims are a further description and are an addition to the detailed description of the present invention.

What is claimed is:

1. A composition comprising at least 50 mole % $C_{20}$ 2-substituted alpha olefins, wherein the $C_{20}$ 2-substituted alpha olefins comprise 2-(3-methylheptyl)-7-methyl-1-undecene, 2-(4-octyl)-7-methyl-1-undecene, 2-(3-methylheptyl)-5-propyl-1-nonene, 2-(2-ethylhexyl)-7-methyl-1-undecene, 2-(3-methylheptyl)-6-ethyl-1-decene, or any combination thereof.

2. The composition of claim 1, wherein the $C_{20}$ 2-substituted alpha olefins comprise 2-(3-methylheptyl)-7-methyl-1-undecene, 2-(4-octyl)-7-methyl-1-undecene, 2-(3-methylheptyl)-5-propyl-1-nonene, 2-(2-ethylhexyl)-7-methyl-1-undecene, and 2-(3-methylheptyl)-6-ethyl-1-decene.

3. The composition of claim 2, wherein the $C_{20}$ 2-substituted alpha olefins comprise at least 10 mole % 2-(3-methylheptyl)-7-methyl-1-undecene, at least 5 mole % 2-(4-octyl)-7-methyl-1-undecene, at least 5 mole % 2-(3-methylheptyl)-5-propyl-1-nonene, at least 5 mole % 2-(2-ethylhexyl)-7-methyl-1-undecene, and at least 5 mole % 2-(3-methylheptyl)-6-ethyl-1-decene.

4. The composition of claim 2, wherein the $C_{20}$ 2-substituted alpha olefins comprise from 20 mole % to 30 mole % 2-(3-methylheptyl)-7-methyl-1-undecene, from 7 mole % to 15 mole % 2-(4-octyl)-7-methyl-1-undecene, from 7 mole % to 15 mole % 2-(3-methylheptyl)-5-propyl-1-nonene, from 7 mole % to 15 mole % 2-(2-ethylhexyl)-7-methyl-1-undecene, and from 7 mole % to 15 mole % 2-(3-methylheptyl)-6-ethyl-1-decene.

5. The composition of claim 2, wherein the $C_{20}$ 2-substituted alpha olefins further comprise 2-(4-octyl)-5-propyl-1-nonene, 2-(4-octyl)-6-ethyl-1-decene, 2-(2-ethylhexyl)-5-propyl-1-nonene, and 2-(2-ethylhexyl)-6-ethyl-1-decene.

6. The composition of claim 5, wherein the $C_{20}$ 2-substituted alpha olefins comprise at least 3 mole % 2-(4-octyl)-5-propyl-1-nonene, at least 3 mole % 2-(4-octyl)-6-ethyl-1-decene, at least 3 mole % 2-(2-ethylhexyl)-5-propyl-1-nonene, and at least 2.5 mole % 2-(2-ethylhexyl)-6-ethyl-1-decene.

7. The composition of claim 6, wherein the $C_{20}$ 2-substituted alpha olefins comprise from 3 mole % to 9 mole % 2-(4-octyl)-5-propyl-1-nonene, from 3 mole % to 9 mole % 2-(4-octyl)-6-ethyl-1-decene, from 3 mole % to 9 mole % 2-(2-ethylhexyl)-5-propyl-1-nonene, and from 2.5 mole % to 8 mole % 2-(2-ethylhexyl)-6-ethyl-1-decene.

8. The composition of claim 5, wherein the $C_{20}$ 2-substituted alpha olefins further comprise 2-(3-methylheptyl)-1-dodecene, 2-octyl-7-methyl-1-undecene, 2-(4-octyl)-1-dodecene, 2-(3-propylheptyl)-1-decene, 2-(2-ethylhexyl)-1-dodecene, 2-octyl-6-ethyl-1-decene, and 2-octyl-1-dodecene.

9. The composition of claim 8, wherein the $C_{20}$ 2-substituted alpha olefins comprise at least 2 mole % of the 2-(3-methylheptyl)-1-dodecene, at least 2 mole % of the 2-octyl-7-methyl-1-undecene, at least 0.5 mole % of the 2-(4-octyl)-1-dodecene, at least 0.5 mole % of the 2-(3-propylheptyl)-1-decene, at least 0.5 mole % of the 2-(2-ethylhexyl)-1-dodecene, at least 0.5 mole % of the 2-octyl-6-ethyl-1-decene, and at least 0.1 mole % of the 2-octyl-1-dodecene.

10. A process comprising: 1) contacting i) a $C_{10}$ olefin composition comprising branched $C_{10}$ olefins, the branched $C_{10}$ olefins comprising 3-propyl-1-heptene, 4-ethyl-1-octene, 5-methyl-1-nonene or any combination thereof, and ii) a dimerization catalyst or dimerization catalyst system; 2) forming a reaction product comprising at least 50 mole % $C_{20}$ 2-substituted alpha olefins; and 3) isolating a composition comprising at least 50 mole % $C_{20}$ 2-substituted alpha olefins, wherein the $C_{20}$ 2-substituted alpha olefins comprise 2-(3-methylheptyl)-7-methyl-1-undecene, 2-(4-octyl)-7-methyl-1-undecene, 2-(3-methylheptyl)-5-propyl-1-nonene, 2-(2-ethylhexyl)-7-methyl-1-undecene, 2-(3-methylheptyl)-6-ethyl-1-decene, or any combination thereof.

11. The process of claim 10, wherein the branched $C_{10}$ olefins comprise at least 8 mole % 3-propyl-1-heptene, at least 6 mole % 4-ethyl-1-octene, and at least 20 mole % 5-methyl-1-nonene.

12. The process of claim 10, wherein the branched $C_{10}$ olefins comprise from 8 mole % to 35 mole % 3-propyl-1-heptene, from 6 mole % to 30 mole % 4-ethyl-1-octene, and from 20 mole % to 65 mole % 5-methyl-1-nonene.

13. The process of claim 10, wherein the dimerization catalyst or dimerization catalyst system comprises i) an alkylaluminum compound, ii) a zirconium compound, or iii) a metallocene compound.

14. The process of claim 13, wherein the dimerization catalyst is the alkylaluminum compound and the alkylaluminum compound consists essentially of a trialkylaluminum compound.

15. The process of claim 13, wherein the dimerization catalyst system is the zirconium compound and an aluminoxane, wherein the zirconium compound comprises zirconium dichloride.

16. The process of claim 13, wherein the dimerization catalyst system is the metallocene compound and (a) an aluminoxane or (b) a non-coordinating anion and an alkylaluminum compound.

17. The process of claim 10, wherein the $C_{20}$ 2-substituted alpha olefins comprise 2-(3-methylheptyl)-7-methyl-1-undecene, 2-(4-octyl)-7-methyl-1-undecene, 2-(3-methylheptyl)-5-propyl-1-nonene, 2-(2-ethylhexyl)-7-methyl-1-undecene, and 2-(3-methylheptyl)-6-ethyl-1-decene.

18. The process of claim 17, wherein the $C_{20}$ 2-substituted alpha olefins further comprise 2-(4-octyl)-5-propyl-1-nonene, 2-(4-octyl)-6-ethyl-1-decene, 2-(2-ethylhexyl)-5-propyl-1-nonene, and the 2-(2-ethylhexyl)-6-ethyl-1-decene.

19. The process of claim 18, wherein the $C_{20}$ 2-substituted alpha olefins further comprise 2-(3-methylheptyl)-1-dodecene, 2-octyl-7-methyl-1-undecene, 2-(4-octyl)-1-dodecene, the 2-(3-propylheptyl)-1-decene, 2-(2-ethylhexyl)-1-dodecene, 2-octyl-6-ethyl-1-decene, and 2-octyl-1-dodecene.

20. The process of claim 10, where the $C_{10}$ olefin composition is substantially devoid of heteroatomic compounds.

21. The process of claim 20, further comprising forming the $C_{10}$ olefin composition substantially devoid of heteroatomic compounds by removing a heteroatomic compound from the $C_{10}$ olefin composition.

22. The process of claim 10, wherein isolating the composition comprising at least 50 mole % $C_{20}$ 2-substituted alpha olefins comprises distilling the dimerization product.

* * * * *